(12) United States Patent
Dangers et al.

(10) Patent No.: US 11,353,451 B2
(45) Date of Patent: Jun. 7, 2022

(54) POC TEST SYSTEM AND METHOD

(71) Applicant: DST DIAGNOSTISCHE SYSTEME & TECHNOLOGIEN GMBH, Schwerin (DE)

(72) Inventors: Marc Dangers, Schwerin (DE); René Rübenhagen, Schwerin (DE)

(73) Assignee: DTS DIAGNOSTISCHE SYSTEME & TECHNOLOGIEN GMBH, Schwerin (DE)

( * ) Notice: Subject to any disclaimer, the term of this patent is extended or adjusted under 35 U.S.C. 154(b) by 579 days.

(21) Appl. No.: 16/233,187

(22) Filed: Dec. 27, 2018

(65) Prior Publication Data

US 2019/0154680 A1 May 23, 2019

Related U.S. Application Data

(62) Division of application No. 14/767,364, filed as application No. PCT/EP2014/053267 on Feb. 19, 2014, now Pat. No. 10,168,324.

(30) Foreign Application Priority Data

Feb. 19, 2013 (EP) .................................... 13155867

(51) Int. Cl.
*G01N 33/543* (2006.01)
*B01L 3/00* (2006.01)
*G01N 33/558* (2006.01)

(52) U.S. Cl.
CPC ...... *G01N 33/54366* (2013.01); *B01L 3/5023* (2013.01); *B01L 3/5027* (2013.01); *B01L 3/50273* (2013.01); *B01L 3/502715* (2013.01); *B01L 3/502723* (2013.01); *G01N 33/558* (2013.01); *B01L 2200/06* (2013.01); *B01L 2200/10* (2013.01); *B01L 2300/0627* (2013.01); *B01L 2300/0636* (2013.01); *B01L 2300/087* (2013.01); *B01L 2300/0809* (2013.01); *B01L 2300/0877* (2013.01); *B01L 2400/049* (2013.01); *B01L 2400/0487* (2013.01)

(58) Field of Classification Search
None
See application file for complete search history.

(56) References Cited

U.S. PATENT DOCUMENTS

| | | |
|---|---|---|
| 2006/0121481 A1 | 6/2006 | Haselton et al. |
| 2008/0057595 A1 | 3/2008 | Schwertner et al. |
| 2009/0211977 A1 | 8/2009 | Miller |
| 2012/0208205 A1 | 8/2012 | Von Olleschikelbheim et al. |

(Continued)

FOREIGN PATENT DOCUMENTS

| | | |
|---|---|---|
| EP | 0063810 A1 | 11/1982 |
| EP | 0171150 A2 | 2/1986 |
| EP | 0246760 A2 | 11/1987 |

(Continued)

OTHER PUBLICATIONS

International Search Report for PCT/EP2014/053267 dated May 13, 2014.

*Primary Examiner* — Bao-Thuy L Nguyen
*Assistant Examiner* — Xiaoyan Zou
(74) *Attorney, Agent, or Firm* — Faegre Drinker Biddle & Reath LLP

(57) ABSTRACT

The present invention relates to a test system or an assay system (detection system) and test method preferably for use in the Point-of-Care (PoC) field.

18 Claims, 5 Drawing Sheets

1 Membrane
2 Test reagent
3 Flow
4 Waste

(56) References Cited

U.S. PATENT DOCUMENTS

2017/0136462 A1 5/2017 Savran

FOREIGN PATENT DOCUMENTS

| EP | 1718970 A2 | 11/2006 |
| EP | 2090365 A1 | 8/2009 |
| WO | WO-8401031 A1 | 3/1984 |
| WO | WO-2005079135 A2 | 9/2005 |
| WO | WO-2006074350 A2 | 7/2006 |
| WO | WO-2010009307 A2 | 1/2010 |
| WO | WO-2011000959 A1 | 1/2011 |
| WO | WO-2013026808 A1 | 2/2013 |

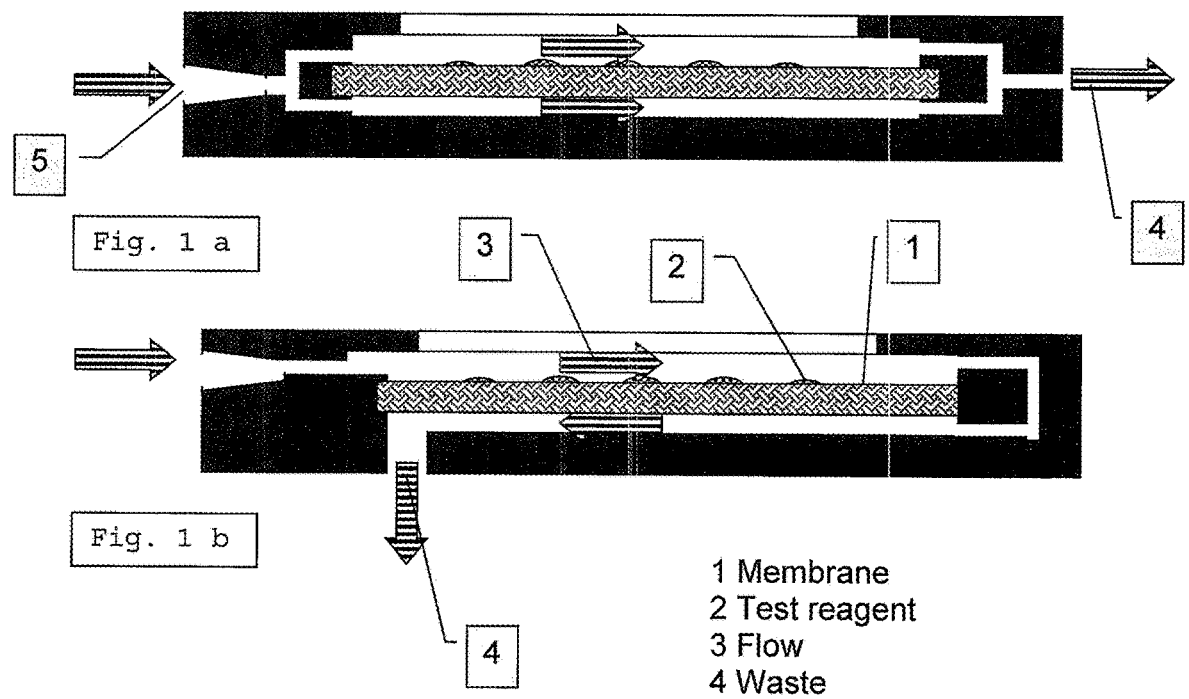
Fig. 1 a
Fig. 1 b
1 Membrane
2 Test reagent
3 Flow
4 Waste
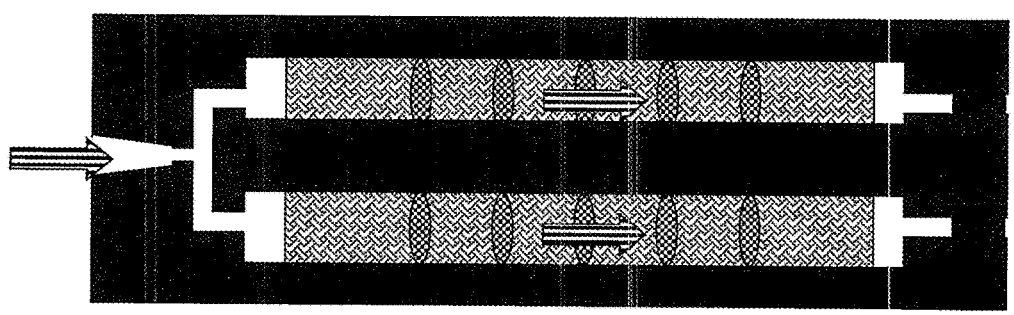
Fig. 2

Track 1    Track 2    Track 3

Front side
Rear side

POC TEST SYSTEM AND METHOD

CROSS-REFERENCE TO RELATED APPLICATIONS

This application is a divisional of U.S. application Ser. No. 14/767,364, filed Aug. 12, 2015 which claims the benefit of national stage application (under 35 U.S.C. § 371) of PCT/EP2014/053267, filed Feb. 19, 2014, which claims benefit of European Application No. 13155867.8, filed Feb. 19, 2013, all of which are incorporated herein by reference in their entirety.

The present invention relates to a test system or assay system (detection system) and test method preferably for use in the Point-of-Care (PoC) field.

In research and in-vitro diagnostics inhuman, veterinary, food, or in a large number of further fields of application, analytical tests are used for the qualitative and/or quantitative determination of molecules, analytes and/or activity or composition thereof. The test results provide different information, such as diagnostic parameters for the identification of diseases, origin of foods, or efficacy of a drug.

Nowadays, the known methods of DNA and protein analysis are the dominant methods among the available tests. In particular, immunoassays are methods in which antibodies are used for the specific binding of selected, sufficiently large target molecules of almost any type, for example biomarkers.

Rapid tests provide measured values within a few minutes or hours following the start of the test, moreover close to the location of sample removal and without the need to send the sample away (Point-of-Care (PoC)).

Known standardised test methods include the lateral-flow test (LFT), flow-through test (FTT), agglutination test (AT) or solid-phase test (SPT). All of these methods detect analytes directly and visually. For tests of this type there are additionally compact readout devices, which also deliver quantitative results.

Known assay methods of in-vitro diagnostics are immunoassays (IAs), in particular enzyme-linked immunoassays (EIAs), or "binding assays" ("sandwich") (for example see EP0171150B1 and EP 0063810B1). In addition, reference is made to the document by Roger P. Ekins (for example WO 8401031 and many others).

Membrane-supported binding assays, in particular of IgE from blood to allergens, have been known since the end of the 1980s, for example from CHEMICAL ABSTRACTS, vol. 101, no. 25, 17, Dec. 1984, page 578, abstract no. 228190b, Columbus, Ohio, US; B. J. WALSH et al.: "Allergen discs prepared from nitrocellulose: detection of IgE binding to soluble and insoluble allergens", & J. IMMUNOL. METHODS 1984, 73(1), 139-45. Some test systems based on the principle of lateral flow are commercially obtainable as rapid allergy tests.

For the PoC field the commercially available Fast-check PoC of the applicant is described by way of example (see EP1718970), which can be used on the basis of a membrane-supported binding assay for allergy detection from whole blood.

Furthermore, a rapid test of the applicant is described in WO2011/000959, in which a membrane is wetted selectively between the detection points in order to introduce the test reagents particularly effectively and in parallel into specific regions of the membrane charged previously with the whole blood to be analysed.

A further rapid test of the applicant is described in WO2013026808A1 of 28 Feb. 2013, wherein fluid is flushed over a membrane from both sides. For this purpose, the membrane is fixed at the longitudinal sides in a device, such that a free volume is created at the upper and lower side of said membrane, through which free volume fluids can flow past the membrane.

There is a great need, however, for improved rapid tests. In particular the uniform charging of the individual detection places with sample fluid (analyte) is capable of improvement, as is an efficient flushing of all detection places, and also a reproducible flow line of the fluids that tolerates the variations of the membrane properties caused by manufacturing tolerances. All of these properties, however, are a precondition for reproducible and high-quality results.

The object of the present invention is therefore to provide, for a PoC test system, an improved and better reproducible method for charging a carrier with sample fluid for the detection of analytes by means of receptor molecules.

This object is achieved surprisingly by the invention. In accordance with the invention a test method for the detection of at least one analyte from a sample fluid is provided, consisting of two sample chambers, which are preferably separated by a carrier, which is partially permeable to a sample fluid and consists of at least two surfaces, wherein a front side of the carrier faces towards the first sample chamber and a rear side of the carrier faces towards the second sample chamber, and a) at least one receptor molecule is fixed on the front side of a carrier,
b) at least one free volume is formed over each of the front side and rear side of the carrier and is delimited in each case by a chamber wall,
c) the first sample chamber has at least two openings, wherein a sample fluid flows through a first opening along a flow gradient over the front side of the carrier to the second opening distanced from the carrier,
d) the second sample chamber has at least two openings, wherein the sample fluid flows through a first opening from the first sample chamber along a flow gradient over the rear side of the carrier and preferably in a direction opposite the flow on the front side of the carrier to the second opening,
e) the second opening of the first sample chamber and the first opening of the second sample chamber are interconnected by a channel,
f) the second opening of the second sample chamber enables the discharge of the fluid,
g) the free volumes from b.) are formed at least partially with a fluid column,
h) wherein the flow gradient along the front and rear side of the carrier is provided by means of pressure application and entrains the fluid column from g.).

This will be referred to hereinafter as the "method according to the invention".

The method according to the invention particularly advantageously allows the reproducible charging and flushing of a carrier with sample fluid for the detection of analytes. Here, a qualitative improvement is obtained by the formation over time of a fluid column along the flow gradients over the carrier and the relevant detection places with the receptor molecules.

In accordance with the invention the carrier preferably separates the two sample chambers, such that practically the entire sample fluid flow between the two sample chambers runs through the carrier or through the channel between the sample chambers, but preferably not beyond the edges of the carrier. It is thus ensured that the upper and lower side even of carriers of varying dimensions are exposed to a flow of the sample fluid to a comparable degree. Any cylindrical curvature of the carrier in the transverse direction, which exists or is created from the outset or only after wetting with the sample fluid, is preferably likewise reduced or even offset by the fastening of the carrier between the sample chambers. This aspect according to the invention also leads to a desired uniform and reproducible flow over the carrier.

In accordance with the invention a channel leads from the second opening of a first sample chamber to the first opening of the second sample chamber. This channel makes it possible for the first time to separate the sample chambers with the aid of the carrier and to still convey the fluid flow from the first to the second sample chamber, such that the front and rear side of the carrier can be exposed to a flow to the same extent. It is surprising that the channel does not influence the flushing effect, although it acts on the flow similarly to a throttle.

A further advantage of this embodiment according to the invention lies in the fact that a return of sample fluid through the channel is prevented in situations in which the pressure applied to the sample chambers is reduced.

In a preferred embodiment this channel from the second opening of a first sample chamber to the first opening of the second sample chamber has a diameter that corresponds approximately to that of the sample feed and of the channel for the rubbish (waste). Furthermore, this channel is preferably smaller in diameter than the diameter of the sample chamber or the free volume. Furthermore, the channel preferably surrounds a fastening element, in particular a transverse strut, of the carrier and has a round bore.

As a result of these aspects it is ensured that, in spite of manufacturing tolerances of the carrier, a sufficient flow gradient with respect to both carrier surfaces, i.e. front and rear side, is created in a reproducible manner, wherein transport of a significant proportion, but at least half, of the sample fluid can be achieved advantageously outside the carrier. This is true particularly for the region of the carrier which is first reached or wetted when the sample fluid flows in and on which at least one receptor molecule is located at a detection place. Other solutions, such as flushing solution, are preferably also transported substantially outside the carrier.

In accordance with the invention the fluid column is formed from the front or rear side of the carrier to the opposite chamber wall of the respective sample chamber (chamber ceiling or chamber base).

In a further preferred embodiment the distance of the first or second surface of the carrier from the chamber wall is 10 μm or more, wherein a fluid column is provided in the free volume over the front side and/or rear side as soon as the flow gradient is produced.

However, a distance from 10 to 1,500 μm (1.5 mm) is preferred between each of the front and rear side and the chamber wall, wherein the flow gradient advantageously cannot stall, a distance from 80 to 350 μm being more preferred, and a distance from 120 μm to 200 μm being particularly preferred.

Furthermore, it may be preferable for both distances of each of the front or rear side of the carrier to be different and in particular to be, for example, 170 μm to the chamber ceiling (top chamber wall) and, for example, 150 μm to the chamber base (lower chamber wall). The variation is dependent on the desired flow gradient depending on the sample fluid.

Furthermore, the carrier is preferably cut to size lengthwise and is securely fastened to the sample chamber on all sides. It is preferable to clamp the longitudinal sides between two edges of the half-shells that form a sample chamber and the free space or free volume above and below the membrane. It is also preferable for one or both end sides of the carrier to be located in a compulsory guide, for example a tab, in order to avoid a shifting of the carrier during the mounting of the test cassette and in order to simplify manufacture. The carrier may likewise be bonded at the longitudinal sides or end sides. A combination of clamping and bonding is also possible. Further possible methods for fastening the carrier include the moulding of the edges in a polymer matrix, solvent bonding, ultrasonic and laser and thermal welding, laser mask welding, mechanical fixing, such as clamping or (plastic) riveting, or 3D printing techniques, in which case the carrier is fixed by the shaping.

In a further preferred embodiment of the invention the test device, besides the two sample chambers, also contains a third chamber, which is fluidically connected to the second opening of the second sample chamber and in which the added fluids (sample fluid, flushing fluid, solutions, etc.) are collected, once they have flowed through the two sample chambers. This third (auxiliary) chamber may be equipped in a known manner with absorbent material, for example cotton wool, cellulose, polyacrylates or functionalised polyacrylates (see FIG. 3 for example). A chamber volume of at least 1.0 ml, in particular 5-10 ml, is preferred.

In a further preferred embodiment the third chamber is connected by at least one opening or vent to the outer side of the test cassette, such that a pressure compensation can be performed by applying pressure to the test cassette. It is particularly advantageous to provide an additional fourth chamber between the third chamber and the outer side of the test cassette so that fluid which exits from the third chamber and for example results from a filling of the test cassette with excessive fluid volumes or from an excessively rapid filling can be collected in the additional chamber and does not pass outwardly, where for example it might come into contact with a user, which is undesirable.

The invention therefore also relates to an embodiment wherein the discharge from the second sample chamber is connected by a channel to a further chamber, wherein this third chamber a) partially contains an absorbent material and
b) contains a vent, which is preferably formed as a channel and particularly preferably as a channel with at least one bend or at least one further chamber.

The leakage of the test fluid may also be prevented by suitable semi-permeable membranes in the further chamber, yet this embodiment nevertheless is much more complex in terms of production.

In a further preferred embodiment the third chamber (the waste container) is connected by a channel to the second sample chamber. A possible capillary draw by the materials in the waste container is thus effectively avoided.

A preferred method for producing the test cassette is the laser beam welding of injection-moulded components, with which a sufficient precision can be achieved in a reproducible manner. It has surprisingly been found that a method in which 3 layers of structured injection-moulded elements (upper half-shell, middle part, lower half-shell) are used, between each of which, prior to the welding, a film provided partially with cutouts or holes is placed, is best suited. The manufacturing complexity appears initially to be greater as a result of the two films, and the method consequently initially appears to be less favourable. However, the complexity and precision to be achieved of the injection-moulded parts can surprisingly be reduced with this method.

An embodiment in which the films are provided with cutouts or tabs, which facilitate the fixing of the carrier prior to the welding, or with holes in order to enable vertical channels, is particularly preferred.

A further preferred method for producing the test cassette is 3D printing, which is particularly suitable for the manufacture of small quantities.

In a further preferred embodiment of the invention the sample fluid is not applied directly to the carrier, but is input into the sample chamber under application of pressure via a (sample) channel in the test device or is sucked in by means of negative pressure. In a preferred embodiment the (sample) channel is oriented parallel to the carrier or in the direction of the flow gradient to be formed. The invention therefore also relates to a method, wherein sample fluid is input into the sample chamber under application of pressure via a (sample) channel in the test device or is sucked in by means of negative pressure, wherein the sample channel leads into the first opening of the first sample chamber (see FIG. 3, for example), wherein a sample fluid flows through this first opening along a flow gradient over the front side of the carrier to the second opening distanced from the carrier.

In a preferred embodiment a diffuser is located at the inlet of the first free volume, as a result of which the fluid flows better over the carrier at the edges.

In a further preferred embodiment the carrier is fastened to the chamber wall in such a way that the pre-existing curvature or the curvature created only after wetting with a fluid points towards the upper side (see FIG. 5).

The use of sample volumes or solution volumes that are greater than the fluid volume that can be received by the carrier or that are greater than the total volume of the carrier in the moist state (see the examples) is also preferred.

The flow gradient can be generated by means of an application of pressure, wherein the sample fluid is exposed to pressure in the sample chamber. A suitable pressure application can be generated manually, in particular by a syringe, ampoule, or by machine, in particular by a pump or a bellows.

An exemplary suitable flow gradient can be achieved as follows:

A sufficient pressure application is, for example, 150 hPa over the chamber, with a typical sample fluid volume of 95 µl, if the height of the free volume is 320 µm, its width is 3.5 mm, its length is 50.5 mm, and the sought filling time is 5 s. With a tenth of the filling time, i.e. 0.5 s, the necessary pressure is approximately 10 times, i.e. 1,500 hPa, under otherwise identical conditions. If negative pressure is applied to the outlet opening, the filling time is at least 0.75 s under otherwise identical conditions.

A further preferred average flow rate of the sample fluid in the chamber is 0.1 m/s, which for example can be comfortably achieved manually by a 1,000 µl disposable syringe with 4 channels and corresponds to a filling period of 5 s (see the example).

Furthermore, in the case of a sample fluid for example having a volume of 95 µl, the free volume over the carrier preferably has a length of the carrier of 50 mm and a width of 3.5 mm, with an overall height of 320 µm (chamber base to chamber ceiling), wherein the distance from the first surface to the chamber ceiling is 170 µm and the distance from the second surface to the chamber base is 150 µm.

The maximum overpressure or negative pressure and flow resistance of the sample chamber is likewise to be dimensioned, with other dimensions of the sample chamber and of the carrier, such that a sample fluid reaches the outlet opening in accordance with the method according to the invention in less than 5 seconds, preferably in less than 2 seconds.

It is also advantageous that the diameter of the inlet opening with a set sample fluid volume for example of 95 µl is 0.3 mm, and that of the outlet opening is 1.2 mm, wherein the distance on the carrier at the given flow rate is preferably 50.5 mm. Other dimensions can be extrapolated accordingly on the basis of the further preferred embodiments.

The invention therefore relates in a preferred embodiment to an optimised sample chamber with an input of a sample fluid of 80-120 µl, wherein the length of the carrier is 40-60 mm, the width of the carrier is 2.0-5 mm, and the inlet diameter is 0.15 mm to 0.45, the outlet diameter is 1 mm to 1.5 mm, and the overall height of the sample chamber is 260 µm to 450 µm.

In further embodiments the flow gradient can be guided selectively a.) in parallel on the first and second surface of the carrier or can be guided b.) antiparallel on the first and second surface of the carrier (see FIGS. 1a and 1b).

An embodiment in which the flow is first guided along the front side of the carrier, through a further channel from the front side of the carrier to the rear side thereof, and subsequently in the opposite direction to a further opening of the second free volume (FIG. 1b) is particularly advantageous. In this embodiment the flow is not divided, but the flow is guided along both sides of the carrier. There is a small risk of a flow inhomogeneity at the bifurcation. In addition, in the case of this embodiment, the flow rate of the solution is twice as high with constant volume of the sample chamber as is the case in an embodiment with identically directed flow. With constant volume of used fluid, an improved flushing effect is additionally achieved on account of the higher flow rate.

In accordance with the invention a test method for the detection of at least one analyte from a sample fluid is provided, consisting of two sample chambers, which are preferably separated by a carrier which is partially permeable to a sample fluid and which consists of at least two surfaces, wherein a front side of the carrier points towards the first sample chamber and a rear side of the carrier points towards the second sample chamber, and a) at least one receptor molecule is fixed on the front side of a carrier,
b) at least one free volume is formed over each of the front side and rear side of the carrier and is delimited in each case by a chamber wall,
c) the sample fluid is divided into the sample chambers via a channel branching into two channels, wherein each leads into a respective one of the two sample chambers, wherein the sample fluid flows in each case through a first opening along a flow gradient over the front and rear side of the carrier to a second opening distanced from the carrier,
d) the second opening of each of the sample chambers transitions in each case into at least one channel, which enables the discharge from the sample chambers,
e) the free volumes from b.) are formed at least in part with a fluid column,
f) wherein the flow gradient along the front and rear side of the carrier is produced by means of pressure application and entrains the fluid column from e.).

In a further preferred embodiment a number of sample chambers (for example 1 to 10) can be connected in parallel and can be fed from a sample channel (see FIG. 2).

The invention therefore relates to a method, wherein a plurality of sample chambers are supplied in parallel from a sample channel with at least one sample fluid.

Within the scope of this invention the term "receptor molecule" means substances such as peptides, proteins, nucleic acids, enzymes, ligands, receptors, antibodies or antigens, DNA, RNA, PNA, and also molecules of non-biochemical origin, such as synthetic molecules. The test reagents may contain combinations of these molecule types or fragments thereof, conjugates thereof, or modified forms thereof, for example glycolised or phosphorylated forms thereof. Lipids and sugars are also included in accordance with the invention. Furthermore, natural substances and natural extracts may be present in test reagents, as is often the case in allergy tests or food incompatibility tests. At least one receptor molecule binds to at least one analyte from the sample fluid. The invention therefore also relates to a binding assay, wherein particularly reproducible results can be obtained by means of the method according to the invention.

In the sense of this invention the carrier consists of a solid material, having a first and second surface, wholly or partially formed of a gel-like, porous, sieve-like, permeable or semi-permeable membrane, dialysis membrane, in particular a coated or uncoated membrane. Exemplary materials include nitrocellulose, PVDF, zeolite, sintering materials, in particular polyethylene oxide, and materials subsequently provided with microchannels, such as silicon, glass or plastics, which have been made permeable by laser drilling, ion bombardment or etching. The carrier may be coated, for example with proteins, in particular antibodies, sugars such as dextrans, or with metals, glass, or plastics, or carbon derivatives such as carbon nanotubes.

In the sense of this invention the expression "the carrier is partially permeable to a sample fluid" means that the sample fluid at least wets the carrier and the sample fluid is partially absorbed at least in the carrier. The possibility that a small amount of the sample fluid will pass through is not ruled out either. Membranes according to the invention are therefore preferred and are commercially obtainable.

The carrier in particular may have two plane-parallel or approximately plane-parallel surfaces, which in accordance with the invention form a front and rear side. In particular the carrier may have the form of a membrane or a flat beam. The carriers may form detection places and may be provided with receptor molecules (test reagents).

One or more receptor molecules are fixed on the first surface of the carrier. Furthermore, at least one receptor molecule may be fixed on a second surface of a carrier. In accordance with the invention, the receptor molecules may also be fixed in a layer beneath the first or second surface. For example, the receptor molecules may be dried up on or close to the surface, either alone or in a stabilising matrix, or may be applied as lyophilisate and detach from the surface during wetting. The fixing may also be provided by use of non-covalent interactions, as exist for example between antibodies and protein A, between biotin and streptavidin, between hexahistidine and nickel NTA, or with the base pairing of DNA. Furthermore, an element of the receptor molecules may be covalently bonded to the first surface. In a preferred embodiment the receptor molecule in the event of wetting remains fixed substantially to the first surface, in particular to an extent of more than 50%.

A sample fluid in the sense of this invention may be any substance or substance mixture, possibly together with solvents, of any origin, but is preferably a biological fluid. The sample fluid may originate in particular from a plant or an animal, in particular from a mammal, in particular from a human. The sample fluid may be, for example and non-conclusively: whole blood, half-blood, serum, saliva, tear fluid, urine, secretion, brain fluid or processed forms of such fluids, or may be fluids containing these aforementioned fluids. The sample fluid may also be diluted. The sample fluid contains at least one analyte that is addressed to at least one receptor molecule or that causes a detectable interaction.

The sample fluid may also contain reagents, such as ligands, competitors, antibodies, in particular with digoxigenin-conjugated antibodies, to which up to 100 anti-digoxigenin antibodies can bind as secondary antibodies and thus amplify the signal, or labelled antibodies, enzymes or enzyme substrates, in particular those that cause a colour change or luminescence, and may contain a second organic sample fluid, which for example contains another antibody and causes a colour change in a further colour.

Furthermore, the sample fluid may contain stabilisers or anticoagulants, such as EDTA, heparin or citrate.

A further solution may also contain detergents, catcher molecules for binding free substances that have not bound to a receptor molecule, or enzyme inhibitors, such that the solution is suitable for flushing or stopping of a reaction.

A solution may contain bidistilled, distilled or mains water with or without further substances, and the water may additionally have passed through an ion exchanger. Furthermore, the solution may contain conventional buffer components for stabilising the pH value or for stabilising components of the sample fluid.

The sample chamber is a cavity in which the carrier is located, and contains both openings (inlet, outlet). The sample chamber may have a shape optimised for manual handling, for example the shape of a flat cuboid, which can be held in a hand. The cuboid is preferably less than 1 cm thick. The fluids may be injected into the sample chamber in succession by means of syringes that are operated using the other hand. The upper side of the sample chamber may contain a transparent cover, which frees the view at least of parts of the carrier and enables a rapid visual assessment of the test in accordance with the method according to the invention. Furthermore, the sample chamber may be designed such that it can be placed in a reader, which contains devices for filling the sample chamber or for reading out the test. Devices of this type, in particular in miniaturised form, may be integrated in a further housing or the like.

The pressure with which the sample fluid flows through an opening into the sample chamber may preferably be generated manually by a syringe, wherein the syringe preferably has a volume that is no smaller than a tenth and is no greater than ten times the sample chamber volume. Furthermore, the syringe preferably has a Luer connection. The fluids may first be drawn up and then injected into the sample chamber using a syringe.

The syringe for pressure generation may also be operated with a syringe pump. Here, it is advantageous that the pressure can be built-up uniformly and in a reproducible manner. In this embodiment a tube connector may be advantageous between the syringe pump and the sample chamber, and the cassette-side end of said connector may be formed as a Luer connection. Furthermore, it may be preferable to provide a valve with at least two paths, such that reagents/sample fluid can be drawn up from one or more storage containers and then delivered into the sample chamber.

The pressure may also be generated in another way manually or by machine, for example by storing the reagents/sample fluid in a compressible storage vessel provided with an opening. The opening may be provided advantageously with a Luer adapter. By manually exerting pressure on the storage device, the test solution passes from the storage container into the sample chamber. The pressure on the storage container may also be generated by machine, for example in that a piston, a lever or a squeezing device presses on the storage vessel, which in turn can be driven pneumatically or hydraulically by means of a motor.

In all methods and devices the pressure application may occur as an overpressure via the inlet opening or as a negative pressure via the outlet opening.

The storage container may be designed for one-time use as a bellows or blister, in particular in pre-filled and closed form. Bellows or blisters made of plastic or film, in particular one-time ampoules, are advantageous. It may be preferable to integrate blisters or one-time ampoules in the test cassette, such that they are produced jointly in the same manufacturing run and the storage containers are pre-filled in a second step.

In a further preferred embodiment of the invention a pump is used that pumps the solutions/sample fluids and feeds these to the sample chamber. The pump may be located between the storage container and sample chamber and may pump the solutions/sample fluids directly, or may pump air or a fluid into a storage container provided with two openings, such that the fluid located therein is displaced and pumped into the sample chamber. Furthermore, a pump may be used that can pump forwards and backwards, and a valve may be used having at least two paths, such that test reagents can be pumped out from one or more storage containers and then delivered into the sample chamber. The pump may also be located after the sample chamber and may generate negative pressure in the sample chamber, such that fluids from a compressible storage container located before the sample chamber are suctioned by negative vacuum into the sample chamber and are optionally suctioned further into the waste container. In this embodiment it is particularly advantageous that the pump is not contaminated with any of the solutions/sample fluids and can therefore continue to be used without cleaning. Micropumps, such as the O-run 100 or O-run 200 by PARIrec GmbH, Gräfelfing, Germany, are particularly suitable. Furthermore, diaphragm pumps and microdiaphragm pumps, peristaltic pumps and gear pumps are particularly suitable.

A fluid, which may be a sample fluid or a solution, flows into the sample chamber with a flow component parallel to the first and second surface of the carrier. If an analyte that can bind to at least one receptor molecule is located in the fluid, this binding is enabled as soon as the fluid is brought into contact with the receptor molecule. Here, it may be preferable, following the introduction of the fluids, to relieve the pressure to approximately atmospheric pressure, such that the fluids are located on the carrier, do not continue to flow or hardly continue to flow, and can incubate and bind receptor molecule and analyte without having to add new fluid. It may also be preferable to reverse the pressure ratio for some time, such that the fluid moves in the reverse direction, or to alternate the pressure conditions for some time, such that the fluid is moved to and fro over the carrier. Compared with unmoved fluid, a better substance exchange is thus possible between fluid and carrier without the need for more fluid.

A further fluid/solution may be used to flush the carrier. When flushing, it may also be preferable to allow the fluid to remain unmoved or to be only slightly moved over the carrier for some time so as to use small fluid quantities. Likewise when flushing, the pressure can be applied in alternation.

It is surprising that a test protocol as described in Example 1 can deliver results that can be read out just as well with the naked eye, such as lateral-flow assays known from the prior art. However, in the case of a lateral-flow assay the fluids flow by means of capillary forces through the carrier and parallel to the surfaces thereof and consequently over the receptor molecules or even through the test/detection fields.

An advantage of the method according to the invention is also that it does not suffer from crosstalk, which may occur in the case of a lateral-flow assay when two receptor molecules located in different test fields bind to the same analyte.

In the case of the method according to the invention the fluid flows over the carrier sufficiently quickly, such that, in the event of contact with the first test reagent, there is no value-falsifying depletion of the analyte from the fluid and there is no influence on the interaction with a second receptor molecule.

A further advantage of the method according to the invention lies in the fact that a plurality of fluids can be added in succession easily, with any time intervals and almost without mixing. By contrast, in the case of a lateral-flow assay this possibility exists exclusively with limitations, since the fluid is moved merely by means of capillary effect of the test strip or the wick pad. Once applied, a fluid moves continuously in the direction of the carrier or wick pad not yet wetted. It is also characteristic for the capillary effect that fluids applied to a carrier at the same time or in succession run into one another and mix together. As a result of this the very sensitive enzymatic test methods, in which a desired signal amplification occurs for example via horseradish peroxidase or alkaline phosphatase, can be carried out merely in a limited manner, for example by drying out. In fact, commercially offered lateral-flow tests are based exclusively on test protocols in which no enzymatic step occurs and in which no more than one liquid reagent is added to the sample.

There are also advantages compared with openly performed tests, in which the test solutions are located in the supernatant over a membrane. In these tests a free membrane or a membrane fixed in a frame is shaken manually in a trough, as is the case in EP1718970 by the applicant, or the trough is moved continuously using a mechanical shaker or rocker shaker. By means of the shaking, a movement of the supernatant relative to the membrane is induced and consequently an improved substance exchange is obtained for the binding reaction, and also for the flushing reaction, which leads to results that are just as good as those obtained with the method according to the invention. The advantages of the closed structure, however, lie in the avoidance of contaminations of the sample, the protection of the user against splashes and contact with the sample fluid, and the independence of operating parameters such as the shaking frequency of the shaker. The reproducibility is therefore improved by methods according to the invention.

It is also surprising that the results are much better when both surfaces of the carrier come into contact with the fluids. This is surprising since the second surface in both cases comes into contact with proportionally similar flows, substance quantities and concentrations of test fluid, reagents and flushing fluids. In an experimental comparison, however, a much poorer flushing effect is observed when the second or rear side of the carrier is secured at the base of the cavity.

The test result can be read out as a result of the fact that the test cassette has a transparent cover, through which the test reagents can be observed and the colour value or grey scale changes can be visually readout. This arrangement also enables a photometric readout of the test method, in particular with use of an optics system, which maps the test results to an image sensor.

This image sensor is preferably a CCD or CMOS sensor. Optics systems from the consumer field, as are used in cameras, web cams and mobile telephones, are particularly economical and yet efficient. In the case of a test with colour change or fluorescence change, it may be preferable to use a colour filter or a colour sensor with colour-sensitive photosensors. With use of fluorescence, the fluorescence can be excited using a lamp, a laser or an LED.

In a further embodiment electrochemical detection methods are used for the readout, as have already been developed in recent years generally for diagnostic methods, for example Dionex ED 40 Electrical Detector User Manual, http://www.dionex.com/en-us/webdocs/4529-34855-03.pdf, Gau, V. et al "Oral Fluid Nanosensor Test (OFNASET) with Advanced Electrochemical-Based Molecular Analysis Platform", Ann. N.Y. Acad. Sci. 1098: 401-410 (2007) doi: 10.1196/annals.1384.005. Wood, M. et al. "eSensor®: An Electrochemical Detection Based DNA Microarray Technology for Multiplexed Molecular Diagnostics" Abstracts of the 219th meeting of the Electrochemical Society (ECS) May 1, 2011-May 6, 2011, Montreal, QC, Canada.

The invention therefore likewise relates to a kit consisting of a test system having two sample chambers, which are separated by a carrier having at least two surfaces, consisting of a sample chamber containing a carrier together with fixed receptor molecules for carrying out a binding assay with an inlet and outlet, wherein a free space exists to the chamber ceiling and chamber base, and optionally a further auxiliary chamber, which is fluidically connected to the sample chamber, together with a means for pressure application, and further auxiliaries and additives, such as stop solution, washing solution, etc. Further embodiments can be provided accordingly as in the above test system/method.

In particular, that the invention therefore relates to a generic kit for the detection of at least one analyte from a sample fluid, comprising two sample chambers, which are separated by a carrier having at least two surfaces, wherein a front side of the carrier points towards the first sample chamber and a rear side of the carrier points towards the second sample chamber, and
  a) at least one receptor molecule is fixed on the front side of a carrier,
  b) at least one free volume is formed over each of the front side and rear side of the carrier and is delimited in each case by a chamber wall,
  (c) the first sample chamber has at least two openings, wherein a sample fluid flows through a first opening along a flow gradient over the front side of the carrier to the second opening distanced from the carrier,
  d) the second sample chamber has at least two openings, wherein the sample fluid flows through a first opening from the first sample chamber along a flow gradient over the rear side of the carrier and preferably in a direction opposite the flow on the front side of the carrier to the second opening,
  e) the second opening of the first sample chamber and the first opening of the second sample chamber are interconnected by a channel,
  f) the second opening of the second sample chamber enables the discharge of the fluid,
  g) the free volumes from b) are formed at least partially with a fluid column,
  h) wherein the flow gradient along the front and rear side of the carrier is provided by means of pressure application and entrains the fluid column from g.).

In particular the invention therefore relates to a generic kit for the detection of at least one analyte from a sample fluid, comprising two sample chambers, which are separated by a carrier having at least two surfaces, wherein a front side of the carrier points towards the first sample chamber and a rear side of the carrier points towards the second sample chamber, and
  a) at least one receptor molecule is fixed on the front side of a carrier,
  b) at least one free volume is formed over each of the front side and rear side of the carrier and is delimited in each case by a chamber wall,
  c) the sample fluid is divided into the sample chambers via a channel branching into two channels, wherein each leads into a respective one of the two sample chambers, wherein the sample fluid flows in each case through a first opening along a flow gradient over the front and rear side of the carrier to a second opening distanced from the carrier,
  d) the second opening in each of the sample chambers transitions in each case into at least one channel, which enables the discharge from the sample chambers,
  e) the free volumes from b.) are formed at least in part with a fluid column,
  f) wherein the flow gradient along the front and rear side of the carrier is produced by means of pressure application and entrains the fluid column from e.).

The invention also relates to the use of the method according to the invention or of a kit or test system (device) for the detection of at least one analyte (substances) from a sample fluid in human, veterinary medical or plant diagnostics, food diagnostics, environment diagnostics, forensic diagnostics, pharmacology, toxicology, in allergies, autoimmune or metabolic diseases, infectious diseases, sexually transmitted diseases, food intolerances, parasitic diseases, determination of small molecules such as drugs, medications or metabolic products, cell mediators, tissue typing, sort typing, food typing, antigen typing, epitope typing and DNA or RNA detection.

Use of the method according to the invention or of a test system (device) in the Point-of-Care field is particularly preferred.

EXAMPLES AND FIGURES

These examples serve exclusively for explanation of the invention and do not limit the invention to these examples.

Example 1

Test Protocol for Allergy Test

Preparation

Bring test box with test tubes and test cassette (kit containing sample chamber) and also the patient sample to room temperature (18-25° C.)

Have ready timer, disposable gloves, container for solid waste and pen.

Remove test cassette and syringe.

All incubations take place at room temperature.

Reinsert, upright, the reagent tubes inserted in the test box (kit), either prior to or following the test procedure, into the correspondingly coloured holding devices at the upper edge of the box.

1.1. Sample Introduction:

Open sample tubes (red cover) containing previously introduced sample and transfer the content completely and bubble-free into the test cassette by means of the syringe. For this purpose insert the syringe into the sample opening and inject the content quickly.

Set down the test cassette on a flat support and incubate for 4 minutes.

1.2. Addition of the Test Solution:

Quickly inject the content of the conjugate solution (yellow cover) as described before (section 10.1.) into the inlet of the test cassette with the aid of the syringe and incubate this, set down, for 8 minutes.

1.3. Washing:

Open the first test tube containing washing solution (blue cover) and quickly inject the content as previously described into the inlet of the test cassette. Then immediately quickly inject the content of the second test tube containing washing solution (blue cover). No incubation is necessary.

1.4. Development:

Open the first tube containing colour substrate (white cover) and quickly inject the content into the inlet of the test cassette. Then immediately open the second test tube containing colour substrate (white cover), inject the content bubble-free into the inlet of the test cassette and incubate this, set down, for 8 minutes.

During the development, 2 parallel reference lines of different intensity and possibly additionally a central test: line are visible in each test field.

1.5. Stopping:

Open test tubes containing stop solution (green cover) and inject the content into the inlet of the test cassette. Note: The test results are stable for at least 12 hours and can be read off during this time.

Example 2

Test Chamber (Sample Chamber)

Dimensions for the membrane and values of the distances thereof from other elements of the device will be specified hereinafter. Here, it should be noted that all dimensions/values are specified for the dry state of the membrane and that a possible deflection of the membrane or surface unevennesses or a potential warping of the injection-moulded parts is not taken into consideration. In the moist state the membrane may swell or deflect and may thus have a modified thickness and modified distances from other components.

A (reinforced) nitrocellulose membrane 140 μm thick is cut to a size of 50.5 mm×6.3 mm. The resultant membrane strip is placed on a film provided with a cutout, such that the strip completely covers the cutout and is clamped at the end sides thereof in each case beneath a tab, said tabs being located at the end-side ends of the cutout in the film. The film is clamped with the membrane strip between two injection-moulded half-shells, which together with the film and the membrane strip form both sample chambers according to FIGS. 1b and 2, of which the width is 3.5 mm. The total volume of the membrane is thus 44.5 μl, and that of the free membrane is 24.7 μl. The distance of the membrane upper side to the substantially planar inner side of the upper chamber wall is 170 μm, and that from the membrane lower side to the substantially planar lower chamber wall of the half-shell is 150 μm. The volume of the upper chamber is 30.04 μl, and that of the lower chamber is 26.51 μl. The cross section of the unclamped part of the membrane is 0.49 mm², and that of the chamber is 1.62 mm².

The chamber is provided with an inlet opening in the first sample chamber in the vicinity of an end of the membrane, which inlet opening has a cross section of 0.3 mm², and with an outlet opening in the second sample chamber in the vicinity of the membrane with a cross section of 1.2 mm².

In the test device 4×2 chambers are formed in parallel, such that the entire membrane volume is 98.98 μl, that of the first chambers without inflow and outflow is 120.19 μl, and that of the second chambers is 106.05 μl. They are filled simultaneously through a single access (sample channel), which fans out into 4 channels, each of which is connected to a first chamber. The outlet openings in turn converge into a single channel, which is connected to a waste volume integrated in the test device, in which waste volume absorbent material is accommodated. The absorbent material is not fluidically connected to any membrane, and therefore the suction effect is limited to free fluid that passes into the waste. The test device has windows, through which the regions of the test strips charged with reagent can be observed.

An opaque film provided with cutouts is bonded to the test cassette. The cutouts serve as windows, through each of which windows the measuring fields each provided for a respective allergen can be viewed or read out using an optical reader. The webs between the windows, which are lined up along a carrier, are kept as narrow as possible, for example 2 mm or less. The webs perpendicularly thereto, from carrier to carrier are wider, such that there is enough space thereon for printed-out information regarding the individual measuring fields. This information may include numbers, acronyms or an entire term, for example designating the allergen.

In a test the following substances and quantities are added in the test device in accordance with protocol 1:

| | |
|---|---:|
| 1) sample together with sample diluent | 380 μl |
| 2) washing bugger per procedure | 1,000 μl |
| 3) substrate solution per procedure (flushing twice) | 2 × 800 μl |
| 4) antibody/conjugate solution 1 | 800 μl |
| 5) antibody/conjugate solution 2 | 800 μl |
| 6) stop buffer | 1,000 μl |

The volume of each individual test component is greater than the volume of the membranes (100 μl).

DESCRIPTION OF THE FIGURES

FIG. 1a: longitudinal section through a test cassette with both sample chambers, in which fluid is guided at both surfaces of the carrier (1) (front side and rear side) in the flow (3) in parallel. The cassette is pressurised through the inlet opening (5), such that the fluid flows from there to the outlet opening and from there through a further channel to the waste (4) (auxiliary chamber (supra)).

FIG. 1b: longitudinal section through a sample chamber, in which fluid flows at the end of the carrier (1) through a further channel and is conveyed to the rear side of the carrier and flows at the second surface (rear side) antiparallel to the first surface.

FIG. 2: Plan view of a sample chamber. A number of carriers may be arranged in parallel in a cassette. For this purpose, the flow may be divided or the carriers may be located jointly in one cavity.

Figure 3:
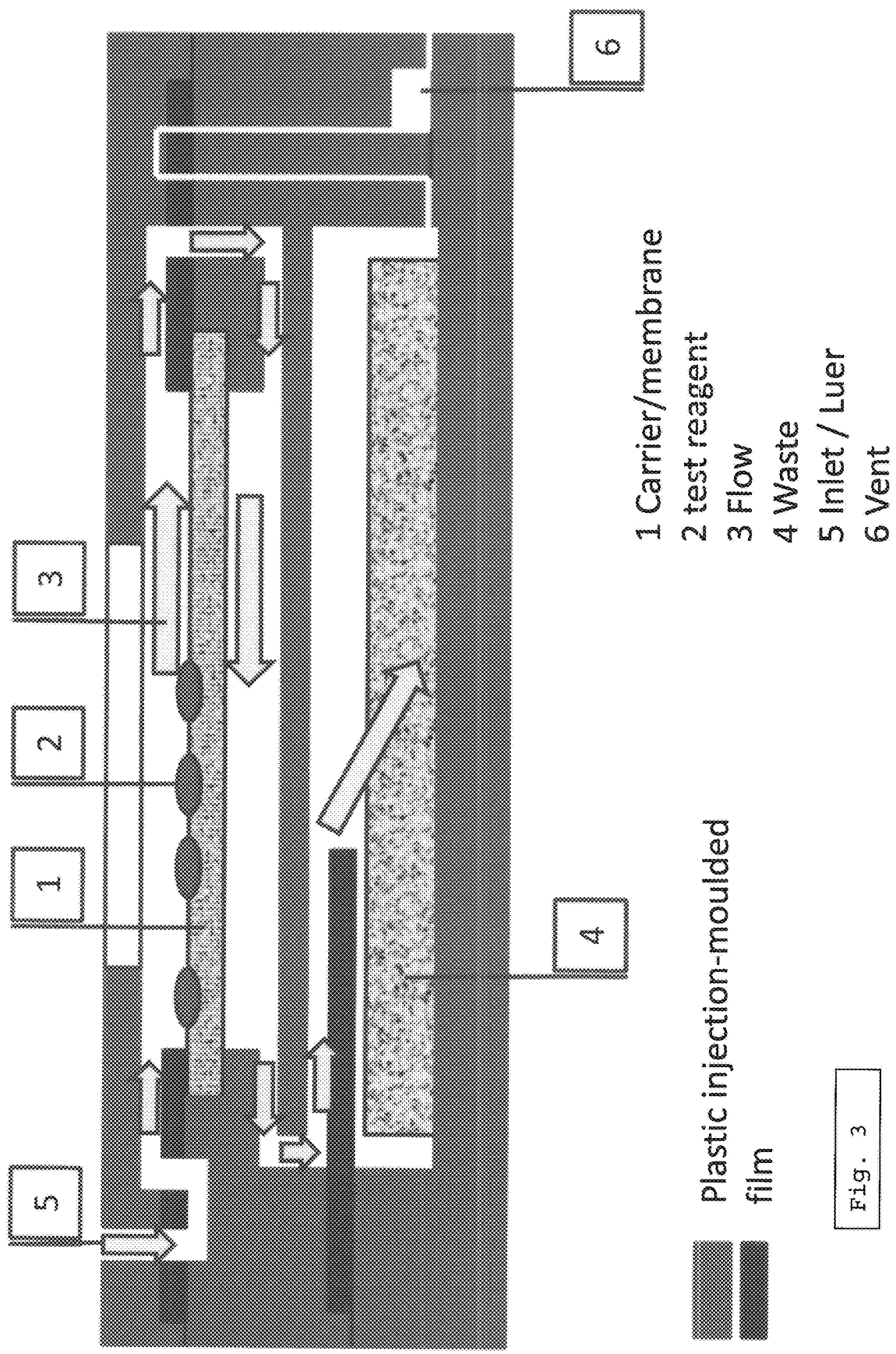
FIG. 3: Detailed longitudinal section of an embodiment, not shown to scale. The solutions are introduced through the inlet opening (5) and flow (3) over the front side of the fixed carrier (1), on which test reagents (2) are located. From there, the solutions pass via a further channel at the other end of the carrier to the rear side of the carrier and flow over this to an outlet opening. An additional channel conveys the fluids to the waste (4), which preferably contains an absorbent material. The chamber for the waste is connected to the outside world via a vent. This vent may be provided with a chicane and further chambers, so as to prevent a leakage of the waste.
Figure 4:
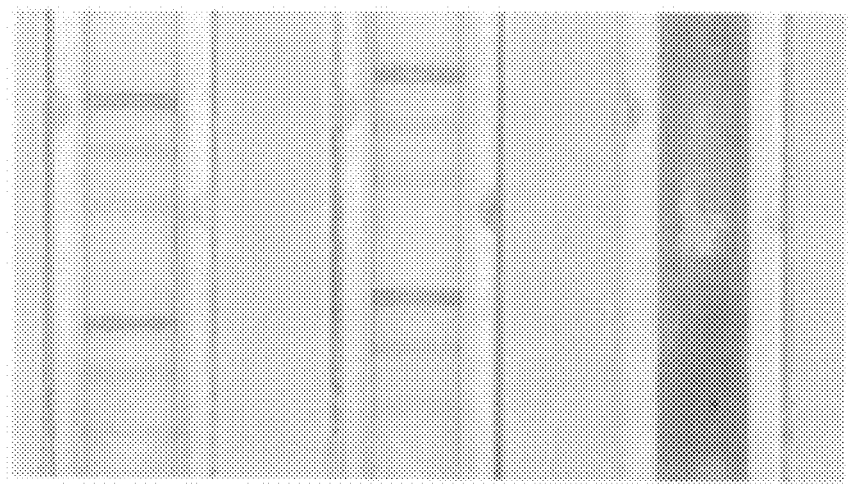
FIG. 4: Immunoassay with three identical membranes as solid phase, performed at the same time in accordance with the protocol from Example 1. In tracks 1 and 2 fluid flows over the membranes from both sides, and in track 3 fluid flows over the upper side only. Identical reagents and volumes were used in all tracks.
Figure 5:
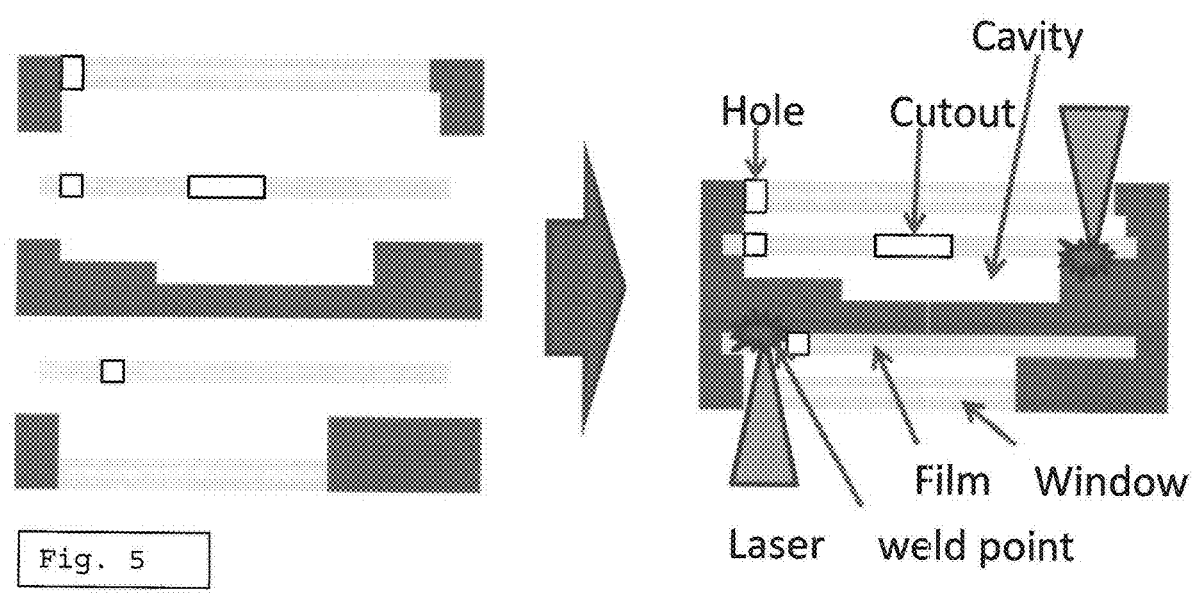
FIG. 5: Longitudinal section as exploded drawing to illustrate the layered structure of the test cassette. The films are located in each case between an injection-moulded half-shell, which is transparent in some regions, and a middle part, which likewise is injection moulded. The laser welds, through the half-shells, the film to the half-shell and middle part, and also welds the half-shells and middle part to one another.
Figure 6:
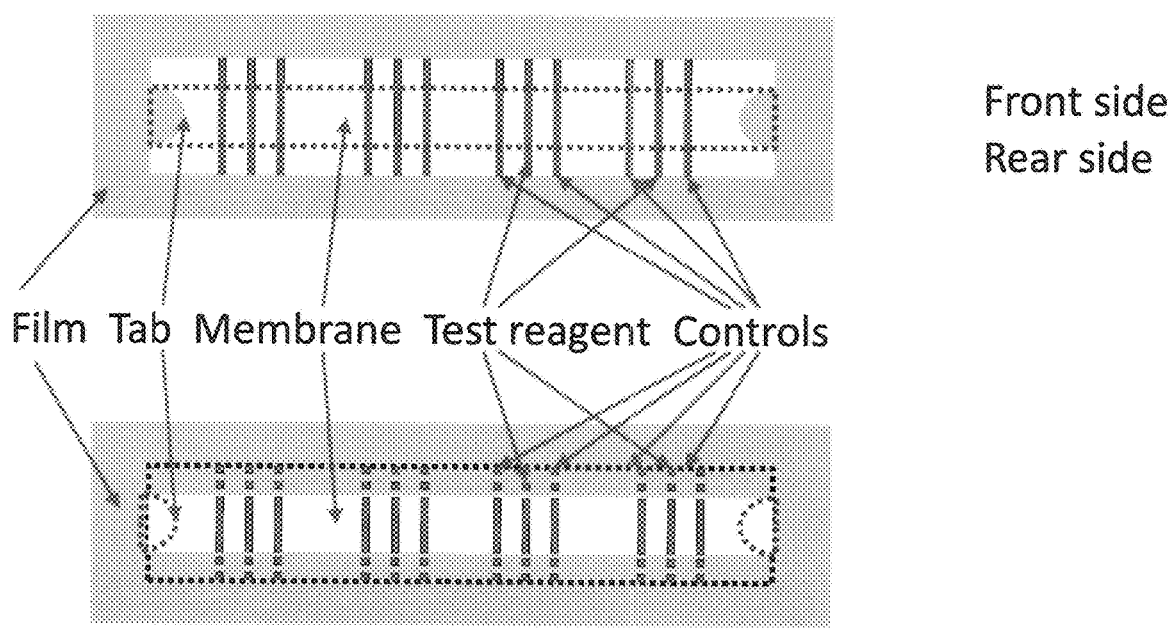
FIG. 6: Detailed plan view of the carrier, not true to scale. The carrier is clamped beneath the end-side tabs of the film and covers the cutout in the film
Figure 7:
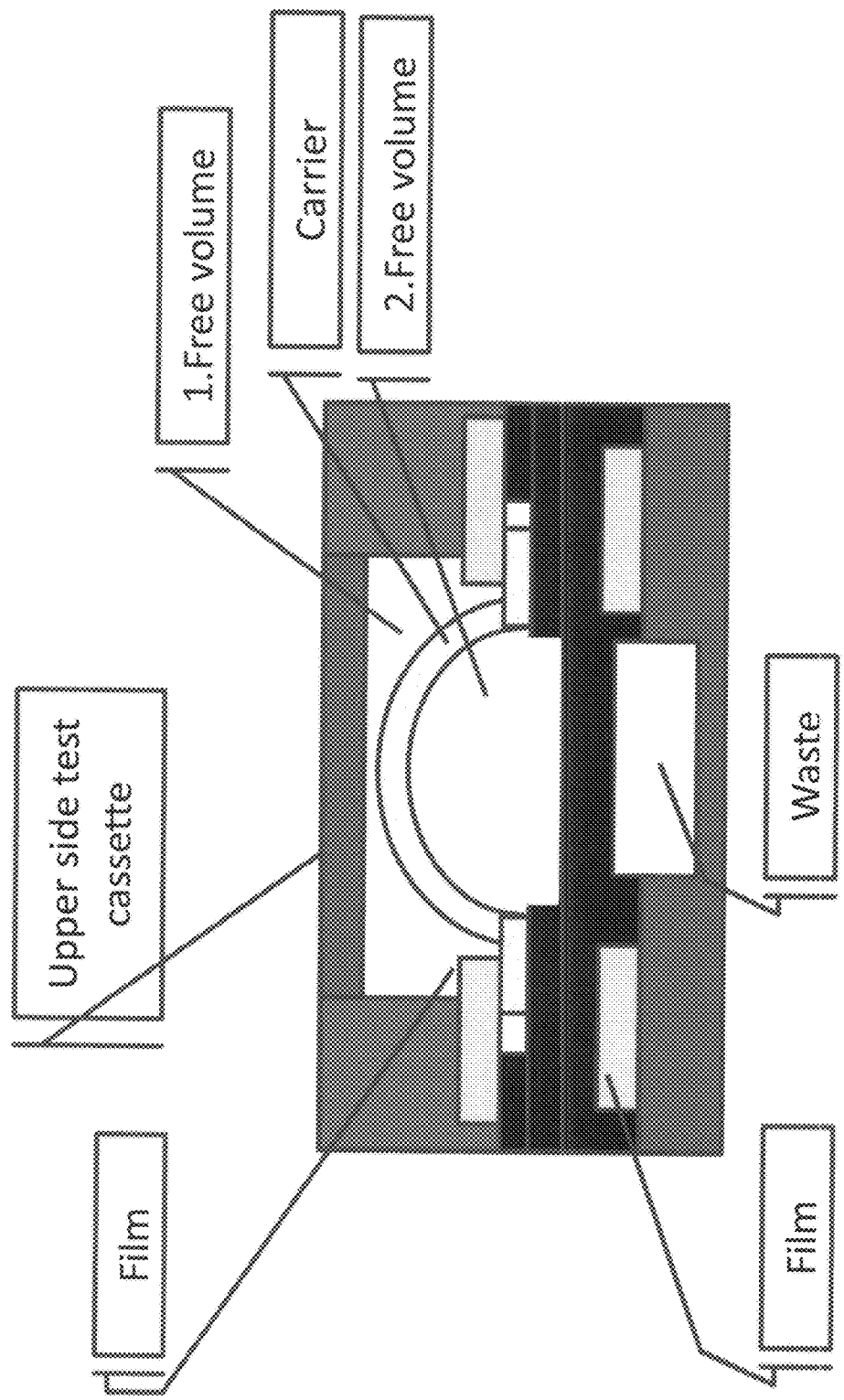
FIG. 7: Cross section through a test cassette, not true to scale. The carrier is fixed at the edges of the sample chambers. Any curvature of the carrier in the transverse direction is shown heavily exaggerated. If a curvature is present or is produced after wetting, the carrier is preferably inserted such that the curvature is formed towards the front side.

The invention claimed is:

1. A test cassette for the detection of at least one analyte from a sample fluid, the test cassette having a first sample chamber and a second sample chamber, which are separated by a carrier having at least two surfaces comprising a front side and a rear side, wherein the front side of the carrier points towards the first sample chamber and the rear side of the carrier points towards the second sample chamber, and
   a) at least one receptor molecule fixed on the front side of the carrier,
   b) at least one free volume formed over each of the front side and the rear side of the carrier and delimiting the free volume in each case by a chamber wall,
   c) the first sample chamber having at least a first opening and a second opening, whereby the sample fluid flows through the first opening along a flow gradient over the front side of the carrier to the second opening distanced from the carrier,
   d) the second sample chamber having at least a first opening and a second opening, whereby the sample fluid flows through the second sample chamber first opening from the first sample chamber second opening along a flow gradient over the rear side of the carrier,
   e) the second opening of the first sample chamber and the first opening of the second sample chamber being interconnected by a channel,
   f) the second opening of the second sample chamber enabling a discharge of the fluid,
   g) the free volumes from b.) being formed at least partially with a fluid column;
   and h) the flow gradient flowing along the front side and the rear side of the carrier by means of pressure application and entraining the fluid column from g.).

2. The test cassette according to claim 1, wherein the carrier is partially permeable to a sample fluid.

3. The test cassette according to claim 1, wherein the channel is smaller in diameter than the diameter of the first sample chamber and the second sample chamber or of the free volume over the front side and the rear side of the carrier.

4. The test cassette according to claim 1, wherein the channel surrounds a fastening element of the carrier with the channel having a round bore.

5. The test cassette according to claim 1, including a third chamber fluidly connected to the second opening of the second sample chamber by a further channel, wherein the discharge from the second sample chamber can flow through the further channel to the third chamber, wherein this third chamber
   a) partially contains an absorbent material and
   b) contains a vent,
   Including a third chamber fluidly connected to the second opening of the second sample chamber by a further channel.

6. The test cassette according to claim 1, wherein the test cassette includes three injection moulded components comprising an upper half-shell and a middle part and a lower half-shell, at least one film is located between at least one of the upper half-shell or the lower half-shell and the middle part, the middle part having at least one cutout and least two tabs for receiving the carrier, a further film located between the middle part and the other of the upper half-shell and the lower half-shell, and the three components are interconnected by laser welding.

7. The test cassette according to claim 1, wherein the distance of the front or rear side of the carrier to the chamber wall is at least 10 μm.

8. The test cassette according to claim 7, wherein the distance is 80 μm to 350 μm.

9. The test cassette according to claim 1, wherein the carrier consists of a solid material, completely or partially formed of a gel, porous, sieve, permeable or semi-permeable membrane.

10. The test cassette according to claim 1, wherein at least one receptor molecule is fixed the rear side of a carrier.

11. The test cassette according to claim 1, wherein the flow gradient is guided a.) in parallel on the first and second surface of the carrier or is guided b.) in antiparallel on the first and second surface of the carrier.

12. The test cassette according to claim 1, characterised in that the pressure application occurs by means of overpressure or negative pressure.

13. The test cassette according to claim 1, characterised in that the carrier has a length of 40-60 mm, a width of 2.0-10 mm, and an inlet diameter of 0.15 to 0.45 mm.

14. The test cassette according to claim 1, characterised in that the first and second sample chambers are part of a plurality of more than two sample chambers.

15. The test cassette according to claim 4, wherein the fastening element is a transverse strut.

16. The test cassette according to claim 5, wherein the vent is an additional channel with at least one bend or at least one additional chamber.

17. The test cassette according to claim 7, wherein the distance is up to 1,500 μm.

18. The test cassette according to claim 8, wherein the distance is 120 μm to 200 μm, and there are different distances of the front side and the rear side of the carrier.

\* \* \* \* \*